USOO5278360A

United States Patent [19]

Carbe et al.

[11] Patent Number: 5,278,360

[45] Date of Patent: Jan. 11, 1994

[54] HEARING AID WAX GUARD WITH INTEGRAL BRIDGE

[75] Inventors: Manfred K. Carbe, Kitchener; Fred J. Stork, Waterloo, both of Canada

[73] Assignee: Unitron Industries Ltd., Kitchener, Canada

[21] Appl. No.: 949,921

[22] Filed: Sep. 24, 1992

[30] Foreign Application Priority Data

Sep. 26, 1991 [CA] Canada ................................ 2052423

[51] Int. Cl.[5] ................................................ A61B 7/02

[52] U.S. Cl. .................................................... 181/135

[58] Field of Search ....................... 181/129, 130, 135; 381/68.6, 69

[56] References Cited

U.S. PATENT DOCUMENTS 4,553,627 11/1985 Gastmeier et al. .................. 181/135

4,870,689 9/1989 Weiss .............................. 181/135 X 5,105,904 4/1992 Olsen .............................. 181/135 X

*Primary Examiner*—Michael L. Gellner

*Assistant Examiner*—Khanh Dang

*Attorney, Agent, or Firm*—Bereskin & Parr

[57] ABSTRACT

A wax guard system, for use with an in-the-ear hearing aid, has a housing secured to the hearing aid shell and an insert which screws into the housing. The insert has a body having an internal passage therethrough, and a bridge extending across the exterior opening of the passage. The bridge is higher at its centre than at its ends and carries a thin domed disk which shields the opening and deters wax from entering the passage.

13 Claims, 4 Drawing Sheets

HEARING AID WAX GUARD WITH INTEGRAL BRIDGE

FIELD OF THE INVENTION

This invention relates to a wax guard insert for use with an in-the-ear hearing aid.

BACKGROUND OF THE INVENTION

The advent of hearing aids which are inserted directly into the user's ear canal has highlighted the problem of ear wax (cerumen) build up. Cerumen produced in the ear canal can damage hearing aids in several ways. Firstly, the wax can build up in the sound spout of the hearing aid and reduce the sound output by a significant amount. When cerumen totally blocks the sound spout the sound output is nil and the hearing aid appears dead.

Secondly, cerumen may migrate through the sound spout and into the hearing aid receiver thereby causing irreparable damage to the transducer and necessitating extensive repair work.

In addition, wax accumulation presents a problem even if the sound spout is only partly blocked because removing the wax from the hearing aid during cleaning may result in wax inadvertently falling down the sound spout into the receiver port.

As a result of the wax build-up and migration problem, various attempts have been made to delay the progress of the wax into the sound spout and receiver port of the hearing aid. Such attempts are shown, for example, in U.S. Pat. No. 4,553,627 filed Oct. 22, 1984, European Patent Application No. 0287315 filed Dec. 4, 1988, and U.K. Patent Application GB2155276A filed Jun. 18, 1984. The above patents show various approaches which have been taken to provide a wax guard for the sound spout of a hearing aid. However these proposals have had only limited success in delaying the progress of wax into the sound spout and receiver port or the hearing aid. The ease of removal and cleaning of the guard is very important given the advanced age of many hearing aid users.

SUMMARY OF THE INVENTION

It is therefore an object of this invention to provide a wax guard system which deters the migration of ear wax into the sound spout of an in-the-ear hearing aid.

In one aspect the present invention provides a wax guard insert for use in a hearing aid shell, said wax guard insert comprising:

(a) a body adapted to be secured to said shell, said body having an outer surface adapted to face outwardly of said shell and an inner surface adapted to face inwardly in said shell, (b) said body having a passage extending therethrough and through said outer and inner surfaces, so that said outer surface has an opening therein forming part of said passage, (c) and bridge means formed integrally with said housing and extending over said opening, said bridge means shielding at least a part of said opening to deter ear wax from entering said opening.

Further objects and advantages of the invention will appear from the following description, taken together with the accompanying drawings.

Figure 3:
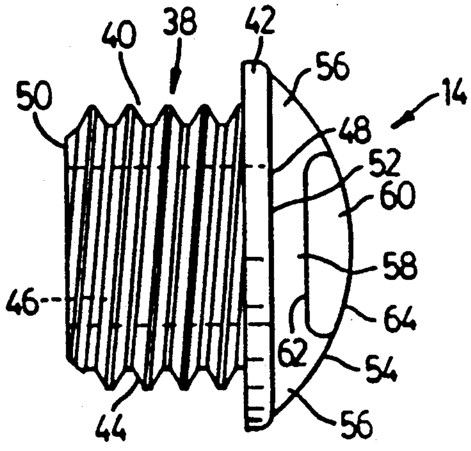
FIG. 3 is an elevation view of an insert for the system of FIG. 1.
Figure 4:
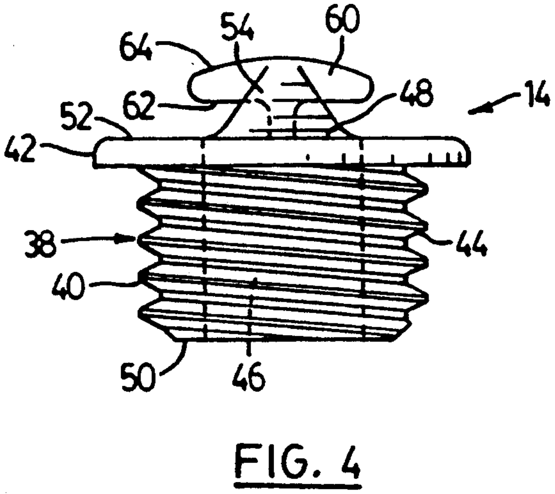
FIG. 4 is another elevation view of the insert of FIG. 3.
Figure 5:
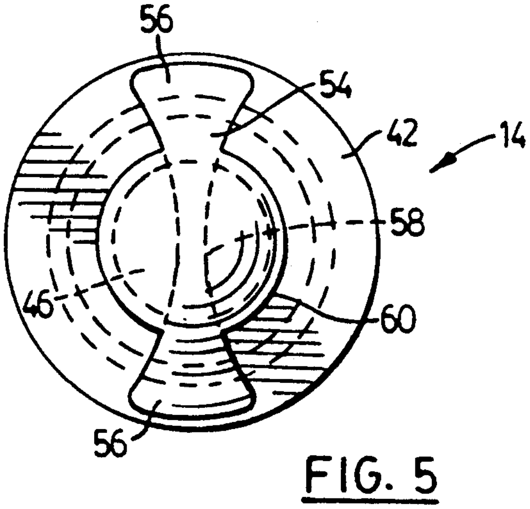
FIG. 5 is a plan view of the insert of FIG. 3.
Figure 8:
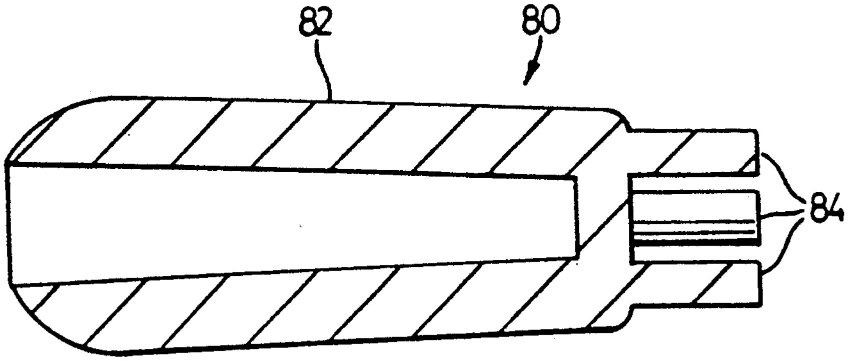
Figure 9:
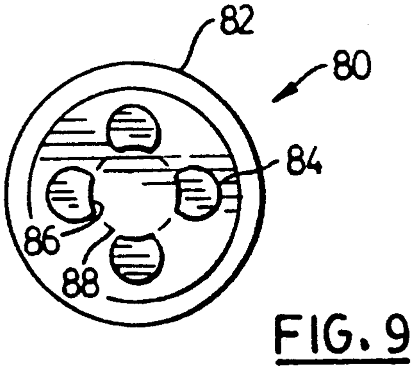

FIGS. *7a* and *7b* show acoustic filters for use in the insert of FIG. 3;

FIG. 8 is a side sectional view of a tool for installing and removing the FIG. 3 insert;

FIG. 9 is an end view of the tool of FIG. 8; and

Figure 10:
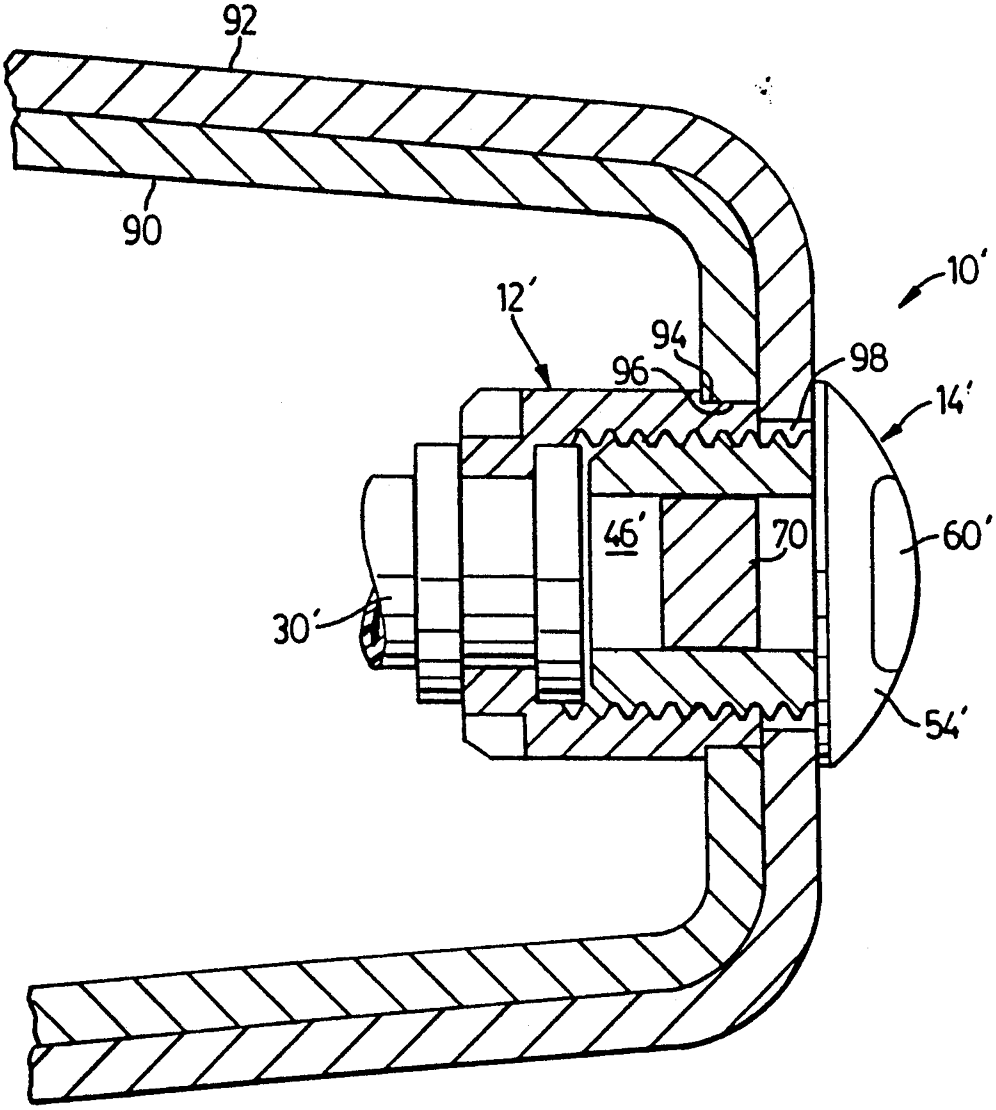

FIG. 10 is a partly sectional view of a modified hearing aid having a wax guard system according to the invention.

DETAILED DESCRIPTION OF PREFERRED EMBODIMENT

Reference is made first to FIGS. 1 to 5, which show a wax guard system 10 according to the invention. The wax guard system 10 consists of a housing 12 and a wax guard insert 14. The housing 12 is located in the canal portion 16 of a hearing aid shell and the wax guard insert fits into the housing 12.

The housing 12 has a generally cylindrical barrel 18 which fits into a corresponding hole 20 in the end of the canal portion 16. The housing 12 also has an outer bevelled flange 22 which seats the housing snugly flush with the outer surface of the canal portion 16 of the shell. The housing 12 is held to the canal portion 16 by glue.

Inside the housing 12 is an internal passage 24 having an internal thread 26. The thread 26 extends from the inner side of flange 22 to a position adjacent an internal flange 28. The internal flange 28 constricts the inner diameter of internal passage 24 at the inner end of the passage. Notches 29 in the exterior of flange 28 aid in removing the housing 12 from a mold.

Inside the canal portion 16, and extending from the housing 12 in a direction toward the interior of the canal portion 16, is a soft tubing 30 having ribs 32 on its outer surface. The ribbed tubbing 30 is attached at its end remote from the housing 12 to a hearing aid receiver (not shown).

To insert the ribbed tubing 30, the wax guard insert 14 must be outside the housing 12. The ribbed tubing 30 is squeezed so that it will fit past the opening in internal flange 28, and then is fed (or pulled) through the housing 12 from the internal flange 28 past the outer flange 22 until the receiver (not shown) is seated at its proper location in the hearing aid. A rib 32*a* of the tubing 30 now engages with the internal flange 28 of the housing 12. The ribbed tubing will extend along past the internal flange 28. Since the tubing 30 is resilient, it is pulled out or stretched slightly past the outer flange 22; the excess is cut off at rib 32*a*, and the tubing then snaps back so that rib 32*a* rests against internal flange 28. The wax guard insert 14 can then be inserted into the housing 12.

The wax guard insert 14 (best shown in FIGS. 3 to 5) comprises an insert body 38 having a cylindrical portion 40 and an outer disk-shaped flange 42. The cylindrical portion 40 has an outer thread 44 which mates to the inner threads 26 of the housing 12. The insert body 38 also has an internal passage 46 which extends therethrough. The passage 46 terminates in an outwardly facing opening 48 in the flange 42, and in an inwardly facing opening at the inner end 50 of the body 38.

Figure 1:
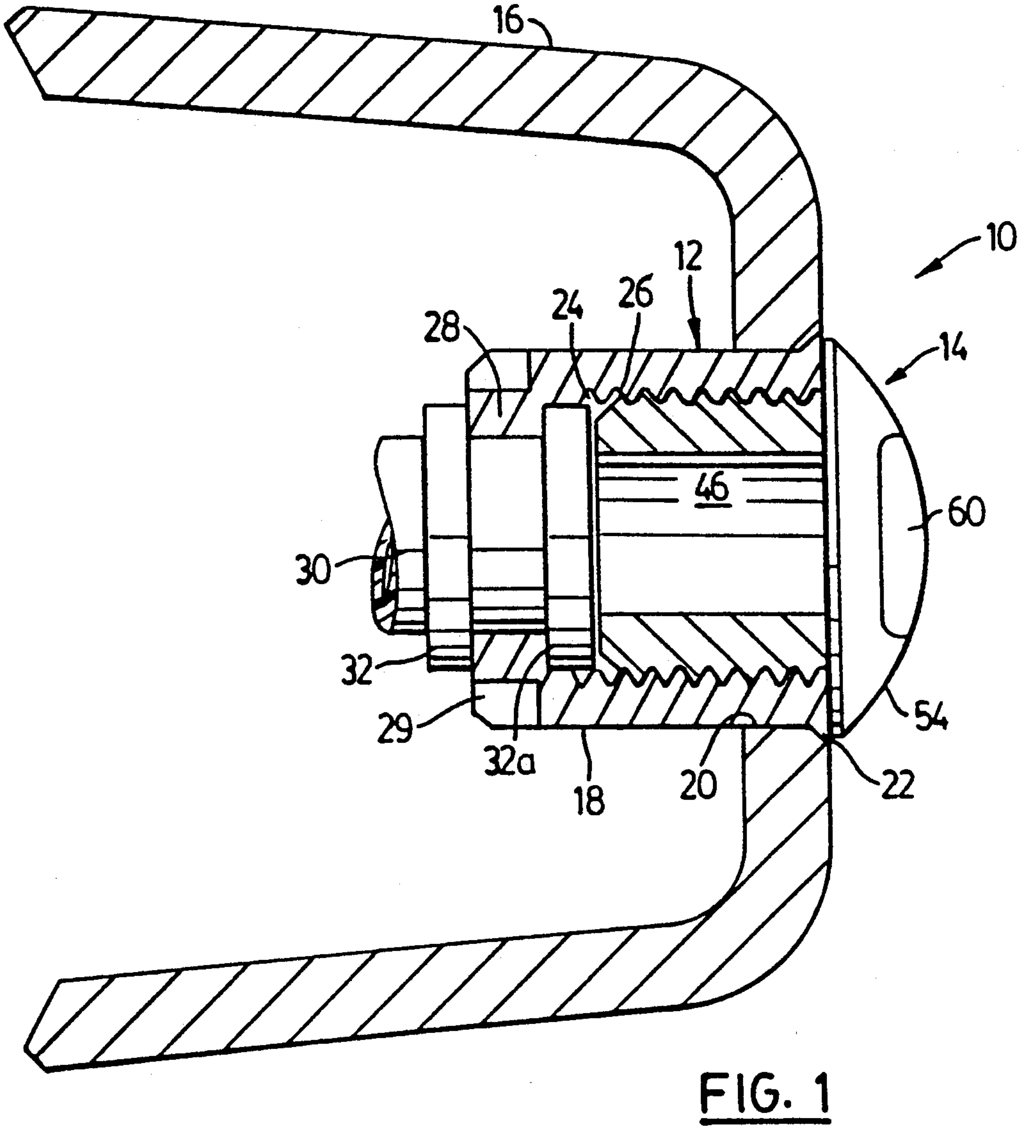
FIG. 1 is a partly sectional view of a portion of a hearing aid having a wax guard system according to the invention.
Figure 2:
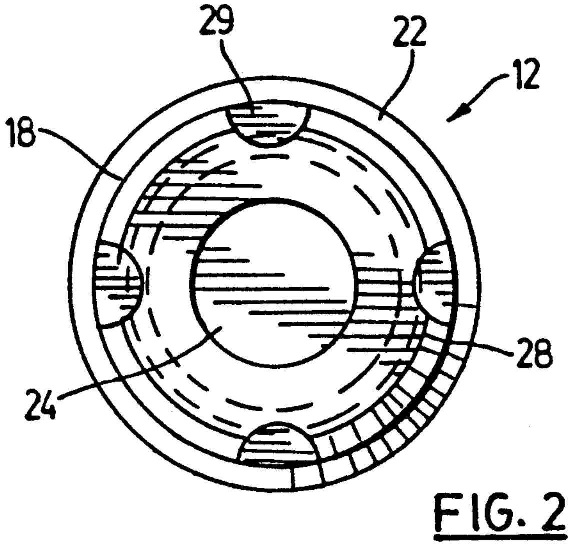
FIG. 2 is a rear view of a housing for the wax guard system of FIG. 1.

The outer surface 52 of the flange 42 carries a bridge 54 which crosses over the opening 48. The bridge 54 is generally of "dog bone" shape as viewed in plan (FIG. 5), having widened ends 56, and having a narrow center 58 where the bridge crosses the opening 48. The bridge 54 is also higher at its center 58 (as best shown in FIGS. 1 and 2) and lower at its ends 56.

At its center 58 the bridge 54 carries a thin domed disk 60. The disk 60 is of slightly greater diameter than that of the opening 48 in flange 42. The inner surface 62 of disk 60 is generally flat, but the outer surface 64 is domed outwardly as shown.

The purpose of the disk 60 is to shield the opening 48 from wax. The disk 48 in effect "ploughs" wax aside as the hearing aid is inserted into an ear. The disk 60 also helps to deter wax from entering the opening 48 after the hearing aid has been inserted into an ear.

While the disk 60 is preferably of slightly larger diameter than the opening 48 it can be of the same diameter, or slightly smaller if desired.

Figure 6:
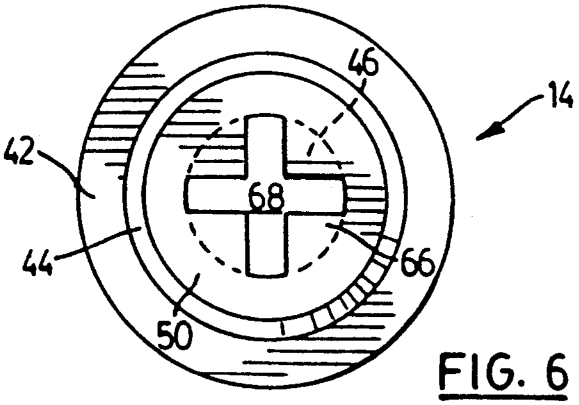
FIG. 6 is a rear view of a modification of the insert of FIG. 3.

While the insert passage 46 has been shown as a "straight through" passage, it can alternatively if desired have a partial obstruction formed at its inner end, as shown in plan view in FIG. 6. As there shown, a plate 66 may be inserted within the passage 46 covering opening 50, but with a cross-shaped opening 68 therein. This additionally helps to deter the passage of wax into the hearing aid.

Figure 7B:
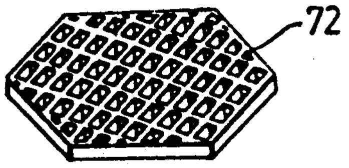
Figure 7A:
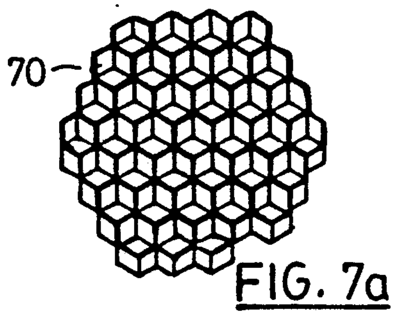

Additionally or alternatively, an acoustic filter can be inserted into the passage 46 to modify selectively the frequency response characteristics of the hearing aid. FIG. 7*a* shows an open cell foam filter 70 which can be press fitted into the passage 46. FIG. 7*b* shows a filter 72 of sintered metal which can be placed in passage 46. Filters 70, 72 attenuate undesired high frequencies and also obstruct the movement of wax through the passage 46.

The entire wax guard system 10 (both the housing 12 and the insert 14) are moulded, typically of nylon or other suitable material. However housing 12 can also be machined.

After the housing 12 has been glued into the hearing aid sound spout, the insert 14 is screwed therein using a suitable tool to grip the disk 60 or bridge 54. If and when the insert 14 becomes plugged with wax, it can be removed (typically by a hearing aid service person) for cleaning or it can be thrown away and a new insert screwed into position since the inserts are extremely small and inexpensive.

FIGS. 8 and 9 show a tool 80 for removing and replacing insert 14. Tool 80 has a handle 82 with four prongs 84 protecting therefrom. The inner surfaces of prongs 84 are concave, as shown at 86, to define an inner circle 88 of diameter slightly less than that of disc 60. Tool 80 is of resilient plastic, so when the prongs 84 are forced over disc 60, the prongs 84 flex or distort slightly outwardly, gripping the disc 60 in a friction fit. Tool 80 can then be turned to screw the insert 14 in or out. The prongs 84 will normally penetrate any wax present on disc 60 or wide grip despite such wax.

FIG. 1 has shown a custom hearing aid shell, i.e. one in which the shell including the sound spout 16 is shaped to fit an individual user's ear canal. If desired, an inner standard or "stock" shell 90 (FIG. 10) can be used which is always of the same shape, so as to fit the hearing aid components in a standard way, with an outer shell 92 whose outer surface is used as a base on which to add material such that the resultant form fits the contours of the user's ear. The system shown in FIG. 10 is essentially the same as that shown and described previously and primed reference numerals indicate parts corresponding to those of previous figures. In FIG. 10, the housing 12' has been slightly modified to eliminate the bevelled flange 28 and instead to provide a reduced diameter portion 94 in the outside surface of the housing 12' at its outer end. The reduced diameter portion accommodates a correspondingly sized hole 96 in the shell 90 and extends through a slightly smaller hole 98 in shell 92. Housing 12' may be secured to shell 90 by glue. Outer shell 92 is secured to inner shell 90 by screwing insert 14 into the housing 12'.

As before, passage 46 can be filled with an acoustic filter of desired acoustic resistance, to selectively modify the frequency response characteristics of the hearing aid. A typical filter is indicated at 70 in FIG. 10.

We claim:

1. A wax guard insert for use in a hearing aid shell, said wax guard insert comprising:
   - (a) a body adapted to be secured to said shell, said body having an outer surface adapted to face in a direction outwardly of said shell and an inner surface adapted to face in a direction inwardly in said shell,
   - (b) said body having a passage extending therethrough and through said outer and inner surfaces, so that said outer surface has an opening therein forming part of said passage,
   - (c) bridge means formed integrally with said body and extending over said opening, said bridge means shielding at least a part of said opening to deter ear wax from entering said opening,
   - (d) said bridge means including bar means extending across said opening, and further including a shielding member connected to said bar means,
   - (e) said bar means having a pair of ends, one on each side of said opening, and a center, said center being higher in said direction outwardly of said shell than said ends.

2. A wax guard insert according to claim 1 wherein said shielding member is a disk-shaped member.

3. A wax guard insert according to claim 2 wherein said disk-shaped member is of diameter greater than that of said opening.

4. A wax guard insert according to claim 3 wherein said disk-shaped member has an outwardly domed outer surface.

5. A wax guard insert according to claim 1 wherein the ends of said bar are wider than the center of said bar.

6. A wax guard insert according to claim 1 and including obstruction means extending into said passage to help deter the movement of wax through said passage.

7. A wax guard insert according to claim 1 wherein said body includes an outer flange adapted to overlie said shell, said flange being of greater diameter than the remainder of said body, said body having exterior threads thereon so that said body may be screwed into a receptacle in said shell.

8. A wax guard insert according to claim 1 and further including a cylindrical housing member, said housing member having an outer surface and an inner passage, said outer surface being adapted to be secured to said shell, said inner surface having interior threads, said body having exterior threads adapted to mate with said interior threads of said housing member so that said insert may be screwed into said housing member, said housing member defining at an inner end of said passage a portion of reduced diameter adapted to trap a ribbed sound tube.

9. A wax guard insert according to any of claims 1 and 2 to 4 and including acoustic filter means in said passage for modifying the frequency response characteristics of a hearing aid in which said insert is placed.

10. A wax guard insert for use in a hearing aid shell, said wax guard insert comprising:

(a) a cylindrical body adapted to be secured to said shell, said body having a substantially flat outer surface of predetermined diameter adapted to face in a direction outwardly of said shell and an inner surface adapted to face in a direction inwardly in said shell, (b) said body having an axial passage extending therethrough and through said outer and inner surfaces, so that said outer surface has an opening therein forming part of said passage, (c) support means formed integrally with said body and located on said outer surface, said support means extending outwardly from said outer surface, (d) a disk-shaped member connected to said support means and extending over at least a substantial portion of said opening, said disk-shaped member being spaced outwardly of said opening and being of smaller diameter than said outer surface of said body, (e) said disk-shaped member having an inner surface facing said outer surface of said body, said inner surface of said disk-shaped member being substantially flat and substantially free of portions extending inwardly toward said outer surface of said body, thus to reduce interference to sound emitted from said passage.

11. A wax guard insert according to claim 10 wherein said disk-shaped member has an outwardly domed outer surface.

12. A wax guard insert according to claim 11 wherein said disk-shaped member is of diameter greater than that of said opening.

13. A wax guard insert according to claim 10, 11 or 12 wherein said support means comprises bar means extending across said opening and bisecting said opening, said disk-shaped member being substantially centered on said bar means.

* * * * *